(12) United States Patent
Artmann et al.

(10) Patent No.: US 12,023,480 B2
(45) Date of Patent: Jul. 2, 2024

(54) METHOD FOR POWER MONITORING AND DYNAMICALLY MANAGING POWER IN A FULLY IMPLANTED LVAD SYSTEM

(71) Applicant: Medtronic, Inc., Minneapolis, MN (US)

(72) Inventors: Joel B. Artmann, Elk River, MN (US); Jacob A. Roe, North St. Paul, MN (US); Jonathan P. Roberts, Coon Rapids, MN (US); David J. Peichel, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 259 days.

(21) Appl. No.: 17/130,197

(22) Filed: Dec. 22, 2020

(65) Prior Publication Data

US 2022/0193393 A1    Jun. 23, 2022

(51) Int. Cl.
 *A61M 60/876* (2021.01)
 *A61M 60/508* (2021.01)
(52) U.S. Cl.
 CPC ........ *A61M 60/876* (2021.01); *A61M 60/508* (2021.01)
(58) Field of Classification Search
 CPC .......................... A61M 60/508; A61M 60/876
 See application file for complete search history.

(56) References Cited

U.S. PATENT DOCUMENTS

| | | | |
|---|---|---|---|
| 3,919,722 A | 11/1975 | Harmison | |
| 4,879,623 A | 11/1989 | Baumgartner et al. | |
| 5,932,979 A | 8/1999 | Sun | |
| 7,915,864 B2 | 3/2011 | Alexander | |
| 8,956,275 B2 | 2/2015 | Boylard et al. | |
| 9,192,772 B1 * | 11/2015 | Tsukamoto | A61N 1/378 |
| 9,789,236 B2 | 10/2017 | Bonde | |
| 2010/0063347 A1 * | 3/2010 | Yomtov | H02J 13/00022 600/17 |
| 2015/0290373 A1 | 10/2015 | Rudser et al. | |
| 2015/0290374 A1 | 10/2015 | Bourque et al. | |
| 2015/0290375 A1 | 10/2015 | Angwin et al. | |
| 2016/0022891 A1 * | 1/2016 | Bluvshtein | A61M 60/585 600/16 |
| 2019/0070350 A1 | 3/2019 | Yomtov et al. | |

OTHER PUBLICATIONS

International Search Report and Written Opinion of International Application No. PCT/US2021/062107, dated Mar. 22, 2022, 14 pp.

* cited by examiner

*Primary Examiner* — Rex R Holmes
*Assistant Examiner* — Jennifer L Ghand
(74) *Attorney, Agent, or Firm* — Shumaker & Sieffert, P.A.

(57) ABSTRACT

In an implanted medical device system, an internal controller, external power transmitter and methods for monitoring and dynamically managing power in an implanted medical device system are disclosed. According to one aspect, an internal controller is configured to provide power to a motor of an implanted medical device, the power being drawn from at least one of an internal battery and an internal coil, the at least one of the internal battery and the internal coil providing a supplied voltage. The internal controller includes processing circuitry configured to switch to one of the internal battery, the internal coil and a combination of the internal battery and the internal coil, based on a comparison of the supplied voltage to a threshold.

10 Claims, 7 Drawing Sheets

METHOD FOR POWER MONITORING AND DYNAMICALLY MANAGING POWER IN A FULLY IMPLANTED LVAD SYSTEM

CROSS-REFERENCE TO RELATED APPLICATION n/a

FIELD

The present technology is generally related to implantable medical devices such as a left ventricular assist device (LVAD), and more particularly to monitoring and dynamically managing power in an implanted medical device system.

BACKGROUND

Referring to FIG. 1, an implantable LVAD system 10 has internal components (in the body of the patient) and external components. The LVAD system 10 may typically include an LVAD pump 12, an implanted controller (i-controller) 14 having an internal battery 15, an implanted internal transcutaneous energy transfer system (TETS) coil (i-coil) 18, an external TETS coil (e-coil) 20 and an external power transmitter 21 with a detachable battery 24. In operation, power is supplied from the external power transmitter 21 to the i-controller 14 via mutual coupling of the coils 18 and 20, in order to charge the internal battery 15 of the i-controller 14 and to power the LVAD pump 12. The coils 18 and 20 transfer power via electromagnetic energy over the air and through the body. The power supplied by the external power transmitter 21 may come from the detachable battery 24 or from a wall outlet, for example.

SUMMARY

The techniques of this disclosure generally relate to monitoring and dynamically managing power in an implanted medical device system.

According to one aspect, an internal controller implantable within a patient and configured to control power supplied to drive a motor of an implanted medical device is provided. The internal controller includes processing circuitry configured to select a power source from one of an internal battery, an internal coil, and a combination of the internal battery and the internal coil, the selecting being based in part on which power source is currently supplying power to the motor. The selecting is further based on at least one of an availability and level of power of the internal coil; and an availability and level of power of the internal battery. The processing circuitry is further configured to set a regulation target voltage to regulate a voltage applied to the motor based on which power source is selected; and regulate the voltage applied to the motor based on the set regulation target voltage and based at least in part on power supplied by the selected power source.

According to this aspect, in some embodiments, the regulating includes tracking a transient signal in the voltage applied to the motor such that a speed of the motor remains within specified limits of a constant value. In some embodiments, the tracking is associated with a latency that is lower than a latency of a proportional integral derivative (PID) controller. In some embodiments, the regulation target voltage is set to a first value to increase efficiency of operation of the internal controller, and is set to a second value higher than the first value to increase power delivery to the motor. In some embodiments, when a rectified voltage from the internal coil is below a voltage of the internal battery and the internal battery is the power source currently providing power, the processing circuitry is further configured to select the internal coil as the selected power source. In some embodiments, when a rectified voltage from the internal coil is above a voltage of the internal battery, the processing circuitry is further configured to select the internal coil as the selected power source, and change the voltage from the internal coil to be lower than the battery voltage.

According to another aspect, a method implemented in an internal controller implantable within a patient is provided. The method includes selecting a power source from one of an internal battery, an internal coil, and a combination of the internal battery and the internal coil, the selecting being based in part on which power source is currently supplying power to a motor of an implanted medical device. The selecting is further based on at least one of: an availability and level of power of the internal coil; and an availability and level of power of the internal battery. The method also includes setting a regulation target voltage to regulate a voltage applied to the motor based on which power source is selected; and regulating the voltage applied to the motor based on the set regulation target voltage and based at least in part on power supplied by the selected power source.

According to this aspect, in some embodiments, the regulating includes tracking a transient signal in the voltage applied to the motor such that a speed of the motor remains within specified limits of a constant value. In some embodiments, the tracking is associated with a latency that is lower than a latency of a proportional integral derivative (PID) controller. In some embodiments, the regulation target voltage is set to a first value to increase efficiency of operation of the internal controller, and is set to a second value higher than the first value to increase power delivery to the motor. In some embodiments, when a voltage from the internal coil is below a voltage of the internal battery and the internal battery is the power source currently providing power, then selecting the internal coil as the selected power source. In some embodiments, when a voltage from the internal coil is above a voltage of the internal battery, the internal coil as the selected as the power source, and the voltage from the internal coil is changed to be lower than the battery voltage.

According to yet another aspect, a motor speed controller in an implanted medical device is provided. The motor speed controller is configured to maintain a speed of a motor of the implanted medical device within predefined limits of a target speed during a transient voltage signal. The motor speed controller includes a first controller configured to produce a first signal indicative of a first difference between the speed of the motor and the target speed, the first controller tracking the first difference between the motor speed and the target speed with a first latency. The motor speed controller also includes a second controller configured to produce a second signal based on a second difference between a target voltage and a supplied voltage and based on the first signal, the second controller tracking the second difference between the target voltage and the supplied voltage with a second latency shorter than the first latency, the second controller being responsive to a transient change in one of the motor speed and the supplied voltage to maintain the motor speed within the predefined limits of the target speed. The motor speed controller further includes a pulse width modulation (PWM) circuit configured to modulate the supplied voltage at a duty cycle determined by the second signal to produce a voltage applied to the motor to drive the motor speed toward the target speed.

According to this aspect, in some embodiments, the supplied voltage is provided by a source selected from an internal battery, an internal coil and a combination of the internal battery and internal coil. In some embodiments, the PWM circuit is configured to increase the duty cycle when the supplied voltage decreases and to decrease the duty cycle when the supplied voltage increases. In some embodiments, when the duty cycle of the PWM circuit exceeds a duty cycle threshold, the supplied voltage is increased.

According to another aspect, an internal controller is configured to provide power to a motor of an implanted medical device, the power being drawn from at least one of an internal battery and an internal coil. At least one of the internal battery and the internal coil provides a supplied voltage. The internal controller includes processing circuitry configured to switch to one of the internal battery, the internal coil and a combination of the internal battery and the internal coil, based on a comparison of the supplied voltage to a threshold.

According to this aspect, in some embodiments, when the supplied voltage is provided by the internal coil and falls below a first threshold, the processing circuitry is configured to switch to the internal battery to supply a higher voltage than the supplied voltage. In some embodiments, when the voltage supplied by the internal coil rises above a second threshold, the processing circuitry is configured to switch to the internal coil to supply the supplied voltage.

According to another aspect, a method in an internal controller configured to provide power to a motor of an implanted medical device is provided. The power is drawn from at least one of an internal battery and an internal coil. The at least one of the internal battery and the internal coil provides a supplied voltage. The method includes switching to one of the internal battery, the internal coil and a combination of the internal battery and the internal coil, based on a comparison of the supplied voltage to a threshold.

According to this aspect, in some embodiments, when the supplied voltage is provided by the internal coil and falls below a first threshold, the method includes switch to the internal battery to supply a higher voltage than the supplied voltage. In some embodiments, when the voltage supplied by the internal coil rises above a second threshold, the method includes switching to the internal coil to supply the supplied voltage.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Some embodiments described herein are related to monitoring and dynamically managing power in an implanted medical device system. For example, some embodiments, are directed toward utilization of pulse width modulation (PWM) to regulate a voltage that controls a motor speed of an implanted LVAD pump 12. This is an improvement over using a DC-DC converter to control motor speed because the DC-DC converter has higher losses and more components than the PWM control of motor speed. To accommodate PWM, a bus voltage is, in some embodiments, dynamically regulated to be between 12 and 18 volts in normal operation to reduce PWM switching losses and other inefficiencies. When higher power is demanded, a higher bus voltage can be used. To operate over a wide range of operating voltages, an internal controller of the implanted medical device system has the ability to disable or disconnect either the internal battery or an external power source. For nominally efficient operation, the battery supply is disconnected while the external power source provides a voltage below the battery voltage. For high power transients, the internal controller can reconnect the internal battery quickly in case the external power source is saturated. To accommodate fast, large transients, fast voltage tracking may be implemented in the motor control circuitry by adding a voltage compensation controller to a motor speed control loop. This voltage compensation controller adjusts the effective voltage at a very fast rate compared to a proportional integral derivative (PID)-governed speed control loop, to maintain a constant motor speed in the presence of fast, large transients. A PWM percentage is monitored as a gauge of power delivery to determine whether to increase or decrease the input voltage, which decreases or increases the PWM percentage, respectively.

Figure 1:
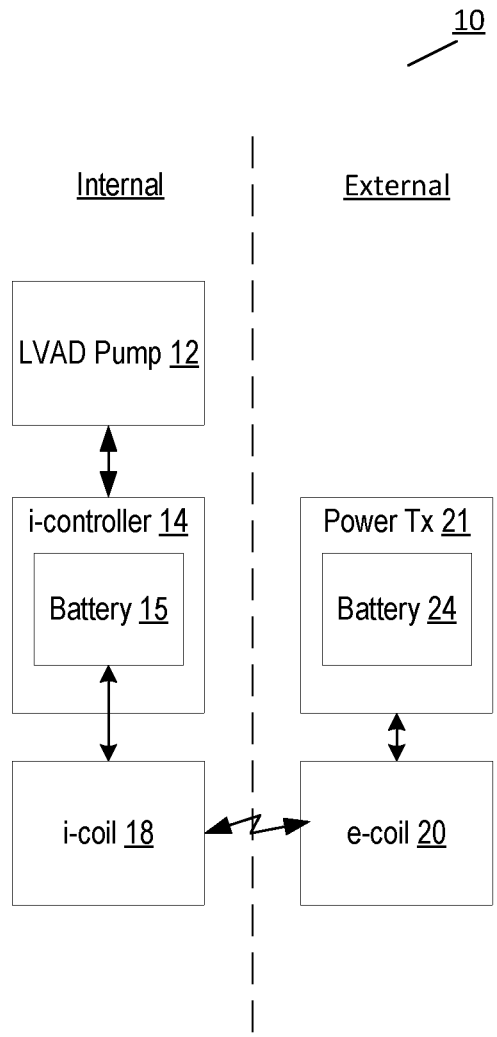
FIG. 1 is a block diagram of an implantable LVAD system.
Figure 2:
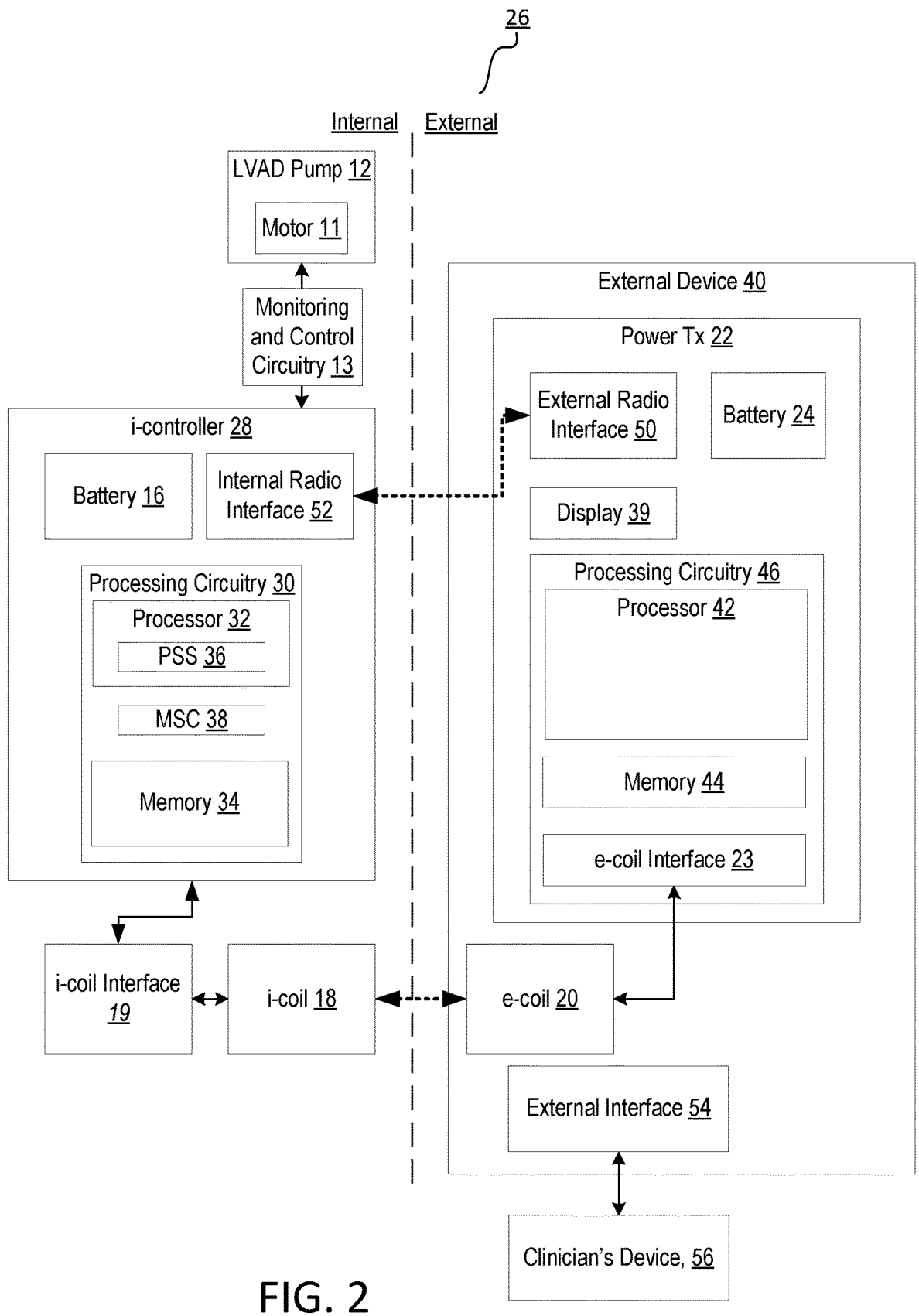
FIG. 2 is a block diagram of an embodiment of an LVAD system that implements a process of monitoring and dynamically managing power in an implanted medical device system.

Referring again to the drawing figures, FIG. 2 shows a block diagram of one example configuration of an implanted medical device system 26 having external components such as an external power transmitter 22, and internal components such as an internal controller (i-controller) 28 configured to perform functions described herein. As used herein, the term "implanted medical device system 26" refers to the system that includes both the implanted/implantable components as well as external components described herein.

The i-controller 28 may have processing circuitry 30 which may include a processor 32 and an internal memory 34. The processor 32 may be configured to execute computer instructions stored in the internal memory 34. Those instructions may include instructions to cause the processor to perform some of the processes described in more detail below. For example, the processor 32 may implement a power source selector 36, which implements a power source selector state machine that transitions between states in which power to the motor 11 of the LVAD pump 12 is provided alternately by the internal battery 16 or the i-coil 18 or by both the internal battery 16 and the i-coil 18. The processing circuitry is also configured to implement a motor speed controller 38 which regulates the speed of the motor 11.

A message or result from the i-controller 28 may be transferred from the i-controller 28 to an external display 39 of an external device 40, which may include a processor 42 and a memory 44 within processing circuitry 46, the external power transmitter 22 and the detachable battery 24, as well as the e-coil 20 in some embodiments. The memory 44 may be configured to store computer instructions to be executed by the processor 42. The external display 39 may be configured to display information received from the i-controller 28.

Electrical communication of signals and power between the internal components of i-controller 28 may be via communication busses and individual electrical conductors not shown in FIG. 2. For example, a multi-conductor address bus and data bus may connect processor 32 with internal memory 34. In some embodiments, an i-coil interface 19 associated with i-coil 18 may be included in the set of internal components making up the implanted medical device system 26. One purpose of i-coil interface 19 may be to modulate the alternating current applied to the i-coil 18 with signals from the i-controller 28 to be transmitted from the i-coil 18 to the e-coil 20 and/or to demodulate signals to be received by the i-coil 18 from the e-coil 20. In some embodiments, a purpose of the i-coil interface 19 is to provide conversion between the alternating current (AC) of the i-coil 18 and direct current (DC) to charge the battery 16.

The power supplied to the i-coil 18 may be adjusted by varying the AC electrical current in the e-coil 20. Some or all functions of the i-coil interface 19 may be included in the i-controller 28 and/or the i-coil 18. In some embodiments, the i-coil 18 and/or i-coil interface 19 may be internal to or considered part of the internal controller 28. Similarly, electrical communication of signals and power between the internal components of external device may be by communication busses and individual electrical conductors not shown in FIG. 2. For example, a multi-conductor address bus and data bus may connect processor 42 with memory 44. In some embodiments, an e-coil interface 23 associated with e-coil 20 may be included in the set of external components making up the implanted medical device system 26. The e-coil interface 23 may include a TETS interface configured to demodulate information signals from the processing circuitry 30 transmitted from the i-coil 18 to the e-coil 20. The e-coil interface 23 may also be configured to couple power from the external power transmitter 22 to the e-coil 20. In some embodiments, the e-coil interface 23 may be two distinct units, one unit for demodulation of signals from the i-controller that are uploaded via the coils 18 and 20, and one unit for coupling power from the external power transmitter 22 to the e-coil 20. In some embodiments, the i-controller 28 may upload information to the external power transmitter 22 via the coils 18 and 20, but the power transmitter does not download information to the i-controller 28 via the coils 18 and 20. As used herein, reference to a TETS power source is a reference to the i-coil 18 power source which is supplied inductively from the e-coil and the external power transmitter 22.

In some embodiments, the internal components of the implanted medical device system 26 may include monitoring and control circuitry 13. A purpose of monitoring and control circuitry 13 may include monitoring speed and temperature, for example, of the LVAD pump 12. Another purpose of the monitoring and control circuitry 13 may include controlling the speed of the LVAD pump 12. Another purpose of the monitoring and control circuitry 13 may include monitoring the temperature of the i-controller 28, the i-coil 18 and/or the implanted battery 16. In some embodiments, some or all of the monitoring and control circuitry 13 may be incorporated into the LVAD pump 12 and/or the i-controller 28. In some embodiments, some or all of the functions performed by the monitoring and control circuitry 13 may be performed by the processing circuitry 30. Thus, in some embodiments, the monitoring and control circuitry 13 may include one or more temperature sensors embedded in the LVAD pump 12, the i-controller 28, the i-coil 18 and/or implanted battery 16. Information obtained from and/or about the LVAD pump 12, such as speed and temperature, may be sent to the external device 40 to be displayed by external display 39. Note that although an LVAD pump 12 is shown, other internal devices may be powered and controlled by the i-controller 28 instead of or in addition to an LVAD pump 12.

The various internal components making up the LVAD system may be grouped into one or more separate housings. Similarly, the various external components making up the LVAD system may be grouped into one or more separate housings. Further, some of the components shown and described as being internal to the i-controller 28 may be instead, external to i-controller 28 in some embodiments. Similarly, some of the components shown and described as being internal to the external device 40 may be instead, external to external device 40, in some embodiments. Note further that some of the functions performed by processor 32 may be performed instead by processor 42.

Note that transfer of information from the external device 40 to the internal memory 34, and vice versa, may be by wireless radio frequency (RF) transmission (over the air and through the body when the i-controller 28 is implanted). Accordingly, in some embodiments, the external device 40 includes an external radio interface 50 and the i-controller 28 includes an internal radio interface 52. In some embodiments, the external radio interface 50 and the internal radio interface 52 are RF transceivers having both an RF receiver for receiving information wirelessly and an RF transmitter for transmitting information wirelessly. Such RF transceivers may be Bluetooth and/or Wi-Fi compliant, for example. In some embodiments, the RF receiver and RF transmitter within the external device 40 or within the i-controller 28 are integrated into one unit, whereas in some embodiments, they could be physically separate units.

Also, information may be communicated to the i-controller 28 from the external power transmitter 22 via the coils 18 and 20, by modulating a parameter of power transmission, such as modulating the frequency of the transmitted power, or by modulating a parameter of the i-coil interface 19, for example, by modulating a tuning capacitance of the i-coil interface 19 or by modulating the load level of the i-controller and/or the i-coil interface 19.

The external device 40 could be a patient's external device that has an external interface 54 which provides an interface between the external device 40 and a clinician's device 56. The clinician's device might, for example, have a USB port and interface 54 might include a USB port, so that a USB cable may connect the two ports. The clinician's device 56 may read data from the external device 40 and write information and control signaling to the external device 40, in some embodiments. In the alternative to a wireline connection, the interface 54 could include or be a radio interface.

Figure 3:
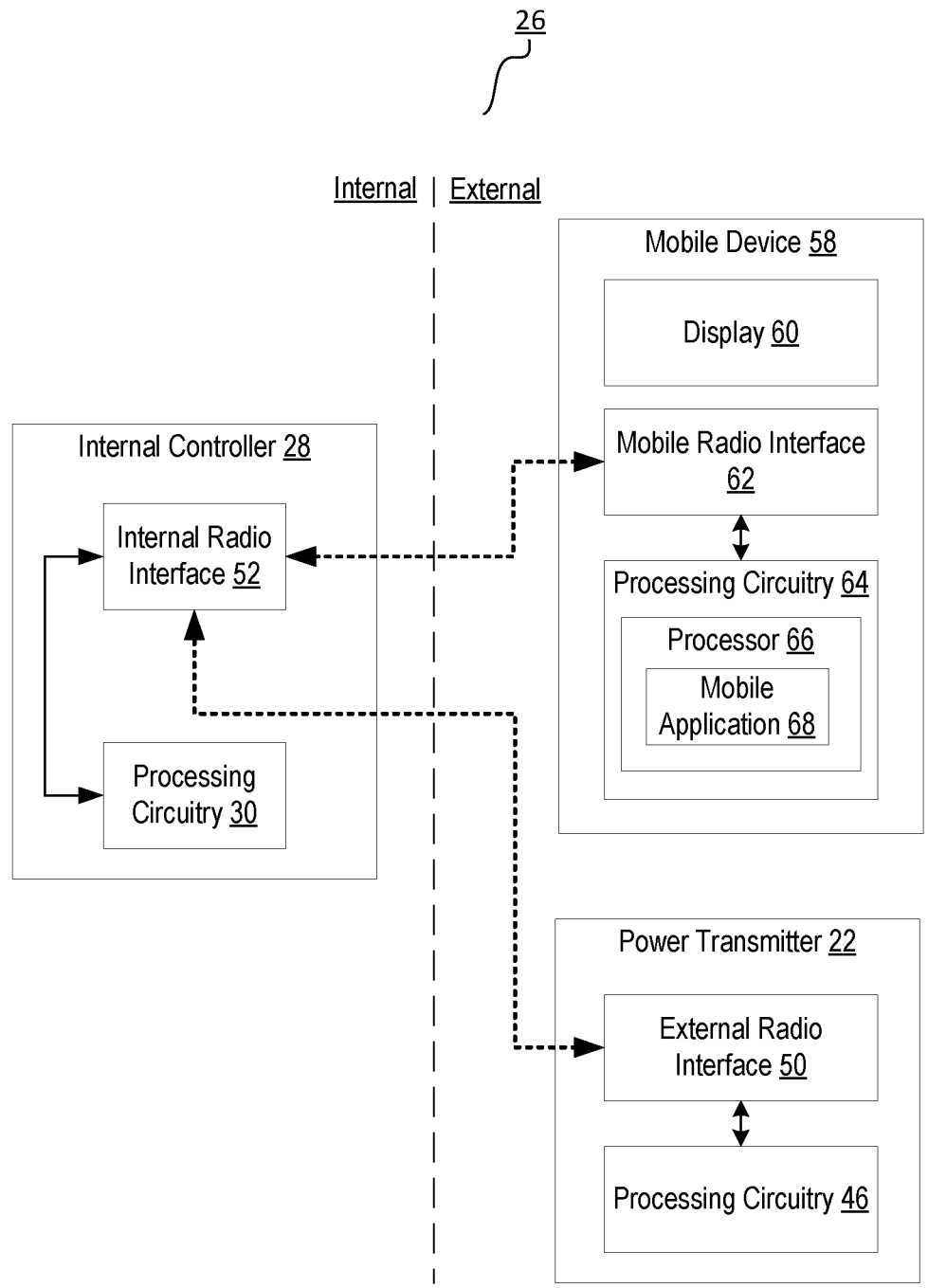
FIG. 3 is a block diagram of an implanted medical device system that includes a mobile device with a mobile application in wireless communication with an internal controller of the implanted medical device.

FIG. 3 is a block diagram of an implanted medical device system 26 that includes a mobile device 58 with a mobile application 68 in wireless communication with the i-controller 28. The mobile device 58 may be a mobile phone or other mobile digital device that can process information and communicate wirelessly with the i-controller. Accordingly, the mobile device 58 has a display 60, a mobile radio interface 62, processing circuitry 64, processor 66 which runs the mobile application 68. The radio interfaces 50, 52 and 62 may be Bluetooth Low Energy compatible radio interfaces, and the i-controller 28 may be a peripheral device responsible for advertising, while the mobile device 58 and the external power transmitter 22 may operate as master or central devices responsible for scanning and issuing connection requests.

Communication from the i-controller 28 to the external power transmitter 22 enables display on external display 39 of implanted device information such as pump data and alarm indications. The i-controller 28 may exchange, via the radio interfaces 50 and 52, diagnostic and log file data with the external power transmitter 22. The i-controller 28 may receive programming commands from an external device such as the clinician's device 56 or mobile device 58. Further, communication from the i-controller 28 to the mobile device 58, via the radio interfaces 52 and 62, enables remote monitoring in cases where the mobile device 58 is connected to the Internet, and enables the display 60 to display information about the state of the implanted portion of the implanted medical device system 26 such as, for example, remaining battery runtime. In some embodiments, the internal radio interface 52 may only communicate with the external radio interface 50 and the mobile radio interface 62 one at a time. In some embodiments, when the i-controller 28 is not engaged in a communication session with an external device, such as external power transmitter 22 or mobile device 58, the i-controller 28 may advertise continually to enable rapid reestablishment of the wireless connection between the i-controller 28 and the external power transmitter 22 or mobile device 58. Conversely, either one or both of the external power transmitter 22 or mobile device 58 may scan for such advertisements.

Figure 4:
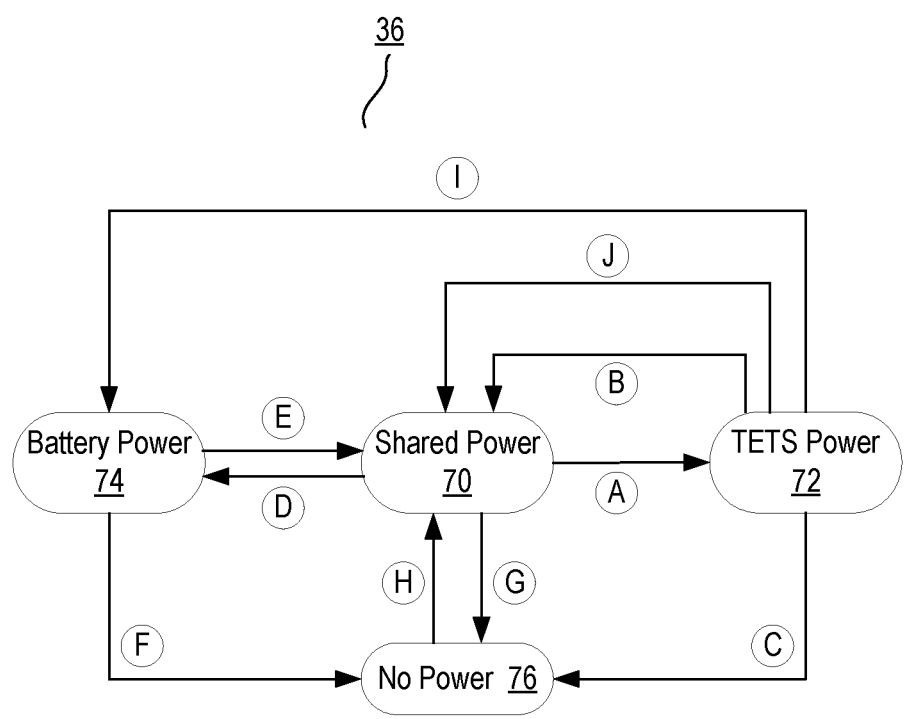
FIG. 4 is a state diagram illustrating states of a power source selector (PSS) state machine.

FIG. 4 is a state diagram that illustrates transitions between different sources of power provided to the motor 11 of the LVAD pump 12. The state diagram of FIG. 4 may be implemented as a finite state machine by the power source selector (PSS) 36 of the processing circuitry 30 of the i-controller 28. In other words, the states of the state machine may be implemented by software executed by the power source selector (PSS) 36. The different states of the PSS 36 are: a shared power state 70, in which power is provided by both the internal battery 16 and the TETS coil 18; a TETS power state 72, in which power is provided by the TETS coil 18; a battery power state 74, in which power is provided by the internal battery 16; and a no power state 76, in which there is no internal battery power available and there is no TETS power available.

Suppose the i-controller 28 is in the shared power state 70 in which power is provided by both the internal battery 16 and the TETS coil 18. Then the i-controller may transition along path A from the shared power state 70 to the TETS power state 72, in which power is provided by the TETS coil 18, when any of the following conditions occur:

TETS power is sufficient to maintain motor speed at a predetermined speed and the internal battery power is greater than a reserve threshold; or TETS power is sufficient to maintain motor speed at a minimum speed and the internal battery power is less than a reserve threshold.

TETS power being sufficient can mean that TETS power is stable over a period of time, there is sufficient PWM % headroom, and a high power threshold is not met.

The i-controller 28 may transition from the TETS power state 72 to the shared power state 70 along path B, when any of the following conditions occur:

A high power threshold is met; or

TETS power is insufficient to maintain motor speed at a predetermined speed and the internal battery power is greater than a reserve threshold; or TETS power is insufficient to maintain motor speed at a minimum speed and the internal battery power is less than a reserve threshold.

When in the TETS power state 72, the i-controller transitions along path C to the no power state 76, when both the following conditions occur:

TETS power is unavailable; and

Internal batter power is unavailable.

The internal battery power 16 being unavailable can mean that an internal battery pack has been disabled due to detection of a temporary or permanent fault condition detected on the state of the battery pack or a battery protection condition having been triggered. Any of these conditions can cause no voltage from the internal battery 16.

In the shared power state 70, the i-controller 28 may transition along path D to the battery power state 74, in which power is provided by the internal battery 16, when both the following conditions occur:

Loss of TETS power; and internal battery power is available.

The i-controller 28 may transition along path E from the battery power state 74 to the shared power state 70, when the following condition occurs:

TETS power is available (this may trigger an unconditional transfer to the shared power state 70).

When in the battery power state 74, the i-controller 28 may transition along path F to the no power state 76 when both the following conditions occur:

TETS power is unavailable; and internal battery power is unavailable.

When in the shared power state 70, the i-controller 28 may transition along path G to the no power state 76 when both the following conditions occur:

TETS power is unavailable; and internal battery power is unavailable.

When in the no power state 76, the i-controller 28 may transition along path H when any of the following conditions occur:

TETS power is available; or

Internal battery power is available.

When in the TETS power state 72, the i-controller 28 may transition along path I to the batter power state 74, when both the following conditions occur:

Internal battery power is available; and

TETS power is unavailable.

When in the TETS power state 72, the i-controller 28 may transition along path J whenever a fault condition exists in i-controller hardware or firmware.

When in the shared power state 70, a TETS power switch may be on, an internal battery power switch may be on, and a regulation target voltage may be set to a first level, such as 18 volts. A default target voltage may set to the first level, e.g., 18 volts.

When in the battery power state 74, an internal battery power switch may be on, a TETS power switch may be on, and the regulation target voltage may be set to the first level, such as 18 volts. The TETS power switch may be on when TETS power is unavailable or when a battery conditioning process is running. In some embodiments, when the battery conditioning process is running, the i-controller 28 may stop sending some or all messages to the external power transmitter 22, and the i-controller 28 may ignore certain messages from the external power transmitter 22.

When in the TETS power state 72, the TETS power switch may be on, the internal battery power switch may be off, and the regulation target voltage may be set to a second level lower than the first level, such as 12 volts. Further, a battery backup voltage level may be set to a third level, such as 10 volts. These voltage levels can be configured by the i-controller 28 or by the external power transmitter 22, in some embodiments. In some embodiments, the voltage supplied by the i-coil 18 (VTETS) may be compared to the battery backup voltage level. The internal battery switch may be enabled when VTETS is less than the battery backup voltage level.

Thus, switching between the TETS power state 72 and the battery power state 74 may occur based on availability of TETS power and internal battery power. For maximum efficiency, the i-controller 28 should operate at a low voltage, for example, 10 volts. In contrast, for maximum power delivery, the i-controller 28 should operate at a higher voltage, for example, 18 volts. For nominal efficient operation when TETS power is below battery voltage, the i-controller 28 can disconnect the internal battery 16 from being the power source for the motor 11. When TETS power is saturated, an internal bus voltage supplying voltage to the motor 11 can experience large voltage transients that can affect LVAD motor speed. To support high power transients, the i-controller 28 can quickly re-connect the internal battery 16 to provide power when TETS power is saturated.

A transient signal is a spurious signal that arises in response to a triggering event. A transient signal may typically rise sharply and then oscillate about a value until the transient signal settles down to the value. Large voltage transients may arise from a backup power management scheme of an internal battery 16, for example. A fast voltage tracking scheme to compensate for these large voltage transients may be implemented in a motor speed control loop.

Figure 5:
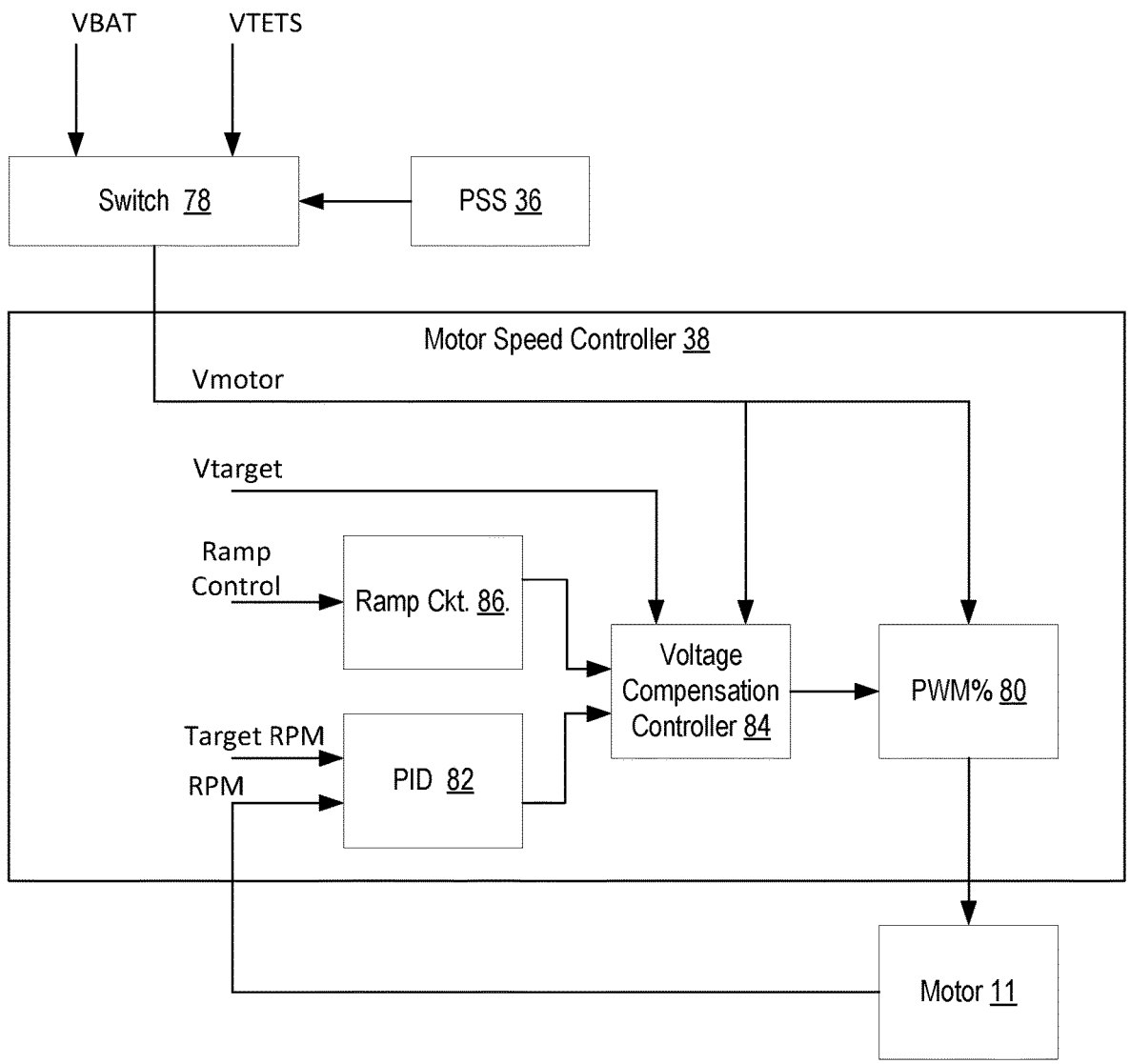
FIG. 5 is a block diagram of a motor speed controller having a voltage compensation controller.

FIG. 5 is a block diagram of elements of a motor speed control loop that includes the motor speed controller 38 and the motor 11. The motor speed is based at least in part on a suppled voltage, Vmotor. The source of the supplied voltage, Vmotor, may be: the internal battery 16, which supplies a voltage VBAT; the i-coil 18, which supplies a voltage VTETS; or a combination of VBAT and VTETS. The source of the supplied voltage, Vmotor, is selected by a switch 78 operating under the control of the power source selector state machine 36.

The motor speed control loop includes a PWM % driver 80 which, by varying the duty cycle responsive to the supplied voltage, Vmotor, determines the effective voltage applied to the motor 11. For example, if the PWM duty cycle is 50%, then the effective voltage applied to the motor 11 is 0.5*Vmotor. By increasing or decreasing the effective voltage applied to the motor 11, the motor speed may be controlled. Vmotor may applied by the i-controller 28 to a voltage bus between the i-controller 28 and the motor 11. The supplied voltage, Vmotor, or a voltage upon which Vmotor is based, may be supplied by the internal battery 16 (battery power state 74) or by the TETS coil 18 (TETS power state 72) or by a combination of the internal battery 16 and the TETS coil 18 (shared power state 70).

The motor speed controller 38 may include a proportional integral derivative (PID) controller 82 and may have inherent latency (phase delay) on the order of 1 millisecond (ms) or more. In the presence of large transients on the voltage applied to the motor 11, the motor speed control loop may not respond quickly enough to maintain a constant motor RPM (revolutions per minute). To address this, a voltage compensation controller 84 is added to the output of the PID controller 82. The voltage compensation controller 84 may cause adjustment of the effective voltage applied to the motor 11 at a very fast rate (on the order of 30 microseconds (us)) as compared to the motor speed control loop latency of 1 ms. This helps maintain constant motor RPM in the presence of large voltage transients and large load transients. A large load transient may be, for example, a transient change in the impedance presented by the LVAD pump 12.

PWM threshold triggering may be employed to detect high power. Operating at a lower supplied voltage, Vmotor, may limit the maximum power that can be delivered to the LVAD pump 12. Monitoring the PWM percent, which may be defined as the ratio of the effective voltage, Vapplied, applied to the motor 11 to Vmotor, is performed to gauge power delivery capability. As the i-controller 28 approaches 100% PWM, the i-controller 28 approaches maximum power delivery capability. Increasing Vmotor reduces the PWM percent and thereby allows for more headroom for power delivery. This technique may be used to indicate that a high power event is occurring so that the i-controller 28 will switch to a higher supply regulation target voltage, Vtarget, or to the internal battery 16.

Assuming the motor is being driven at a constant power, changes in the supplied voltage, Vmotor, may be compensated in the PWM % driver 80 so that the effective voltage applied to the motor 11 remains the same. The majority of the time, Vmotor may be set to a low value such as 10 volts to minimize losses caused by PWM switching. However, this may limit the maximum power that can be delivered to the motor 11. If the PWM duty cycle crosses a duty cycle upper threshold approaching 100%, the supplied voltage, Vmotor, may be increased. The supplied voltage, Vmotor, may be increased by increasing a TETS target voltage, Vtarget, and/or by employing an internal boost converter for increasing a voltage from the internal battery 16.

Generally, when there is a power transient from the motor 11 that is faster than can be supplied by the TETS power from the i-coil 18, the supplied voltage, Vmotor may be pulled down. If Vmotor falls below a motor voltage lower threshold such as 10 volts, the internal battery will quickly be switched in to supply a higher voltage such as 16 volts. When the TETS power recovers, the voltage Vtarget may be set to an even higher level such as 18 volts, or some voltage above the internal battery voltage. The voltage Vtarget may be maintained at this level until the internal battery supply is switched out and the TETS supply is switched in. Once the TETS i-coil 18 is providing power to the i-controller 28, the target voltage, Vtarget, can be reduced to a lower voltage where the efficiency of the i-controller 28 may be higher.

Within the voltage compensation controller 80, the target voltage, Vtarget, may be compared to the supplied voltage Vmotor. When Vmotor is greater than Vtarget, then the signal from the PID 82 may be modified to cause the PWM duty cycle of the PWM % driver 80 to decrease, whereas, when Vmotor is less than Vtarget, then the signal from the PID 82 may be modified to cause the PWM duty cycle of the PWM % driver 80 to increase. An amount of compensation may be expressed as Vtarget/Vmotor. This amount of compensation may be related to a speed of the loop that includes PWM % 80, motor 11, PID 82 and voltage compensation controller 84.

A ramp circuit 86 receives ramp control signals from the processing circuitry 30 of the i-controller 28 which specify parameters of a ramp voltage to initiate the voltage compensation controller 28. The specified parameters may include a start voltage, an end voltage, a voltage step, a ramp direction, etc.

The PID controller 82 receives as one input a measure of RPM of the motor 11 and receives as another input a target RPM. The PID controller 82 may produce an output to the voltage compensation controller 80 that depends at least in part on a difference between the motor RPM from the motor 11 and the target RPM from the processing circuitry 30.

Figure 6:
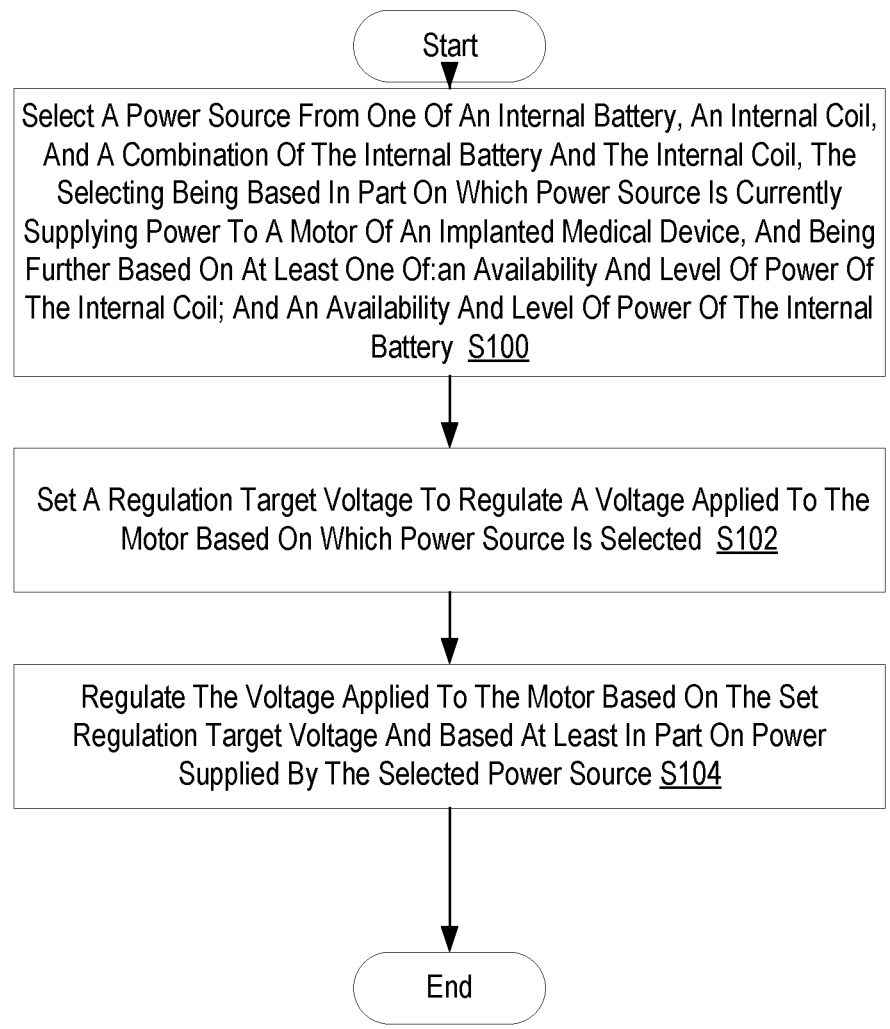
FIG. 6 is a flowchart of a process implemented in an internal controller of an implanted medical device according to principles set forth herein.

FIG. 6 is a flowchart of an example process implemented in an internal controller 28 of an implantable medical device according to principles set forth herein. The process includes selecting, via the processing circuitry 30, a power source from one of an internal battery 16, an internal coil 18, and a combination of the internal battery 16 and the internal coil 18. The selecting is based in part on which power source is currently supplying power to a motor 11 of an implanted medical device, and is further based on at least one of: an availability and level of power of the internal coil 18; and an availability and level of power of the internal battery 16 (Block S100). The process further includes setting, via the processing circuitry 30, a regulation target voltage to regulate a voltage applied to the motor 11 based on which power source is selected (Block S102). The process also includes regulating, via the processing circuitry 30, the voltage applied to the motor 11 based on the set regulation target voltage and based at least in part on power supplied by the selected power source (Block S104).

Figure 7:
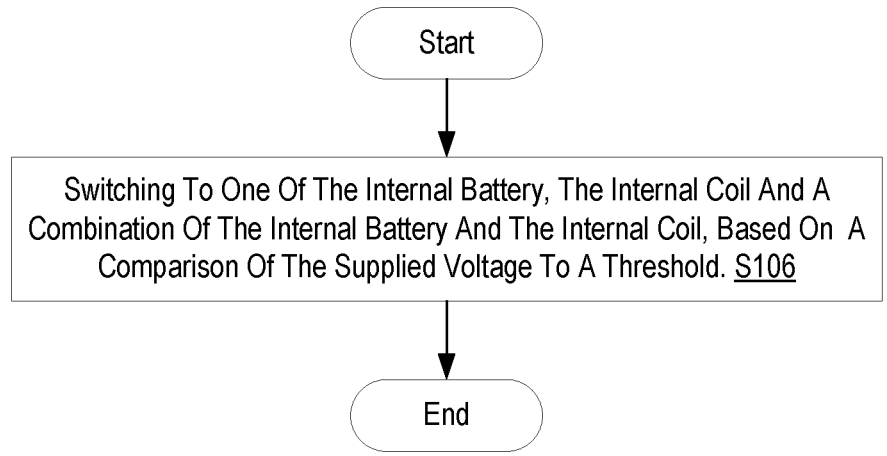
FIG. 7 is a flowchart of a process implemented in an internal controller of an implanted medical device according to principles set forth herein.

FIG. 7 is a flowchart of another example process implemented in an internal controller 28 of an implantable medical device according to principles set forth herein. The method includes switching to one of the internal battery 16, the internal coil 18 and a combination of the internal battery 16 and the internal coil 18, based on a comparison of a supplied voltage to a threshold (Block S106).

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media and memory may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope of the following claims.

What is claimed is:

1. An internal controller implantable within a patient and configured to control power supplied to drive a motor of an implanted medical device, the internal controller including processing circuitry configured to:
    select a power source from one of an internal battery, an internal coil, and a combination of the internal battery and the internal coil;
    set a regulation target voltage to regulate a voltage applied to the motor based on the power source selected; and
    regulate the voltage applied to the motor based on the regulation target voltage and based at least in part on power supplied by the power source, wherein to regulate the voltage, the processing circuitry is configured to:
        track a transient signal in the voltage applied to the motor using a voltage compensation controller of the internal controller and a proportional integral derivative controller of the internal controller, wherein a first latency associated with tracking the transient signal using the voltage compensation controller is less than a second latency associated with tracking the transient signal using the proportional integral derivative controller; and
        regulate a speed of the motor to remain within specified limits of a constant value.

2. The internal controller of claim 1, wherein the processing circuitry is configured to:
    set the regulation target voltage to a first value to increase efficiency of operation of the internal controller; and
    set the regulation target voltage to a second value higher than the first value to increase power delivery to the motor.

3. The internal controller of claim 1, wherein, when a rectified voltage from the internal coil is above a voltage of the internal battery, the processing circuitry is further configured to:
    select the internal coil as the power source; and
    change the rectified voltage from the internal coil to be lower than the voltage of the internal battery.

4. A method implemented by an internal controller implantable within a patient and configured to control power supplied to drive a motor of an implanted medical device, the method including:

selecting a power source from one of an internal battery, an internal coil, and a combination of the internal battery and the internal coil;

setting a regulation target voltage to regulate a voltage applied to the motor based on the power source selected; and regulating the voltage applied to the motor based on the regulation target voltage and based at least in part on power supplied by the power source, wherein regulating the voltage applied to the motor includes:

tracking a transient signal in the voltage applied to the motor using a voltage compensation controller of the internal controller and a proportional integral derivative controller of the internal controller, wherein a first latency associated with tracking the transient signal using the voltage compensation controller is less than a second latency associated with tracking the transient signal using the proportional integral derivative controller; and regulating a speed of the motor to remain within specified limits of a constant value.

5. The method of claim 4, further comprising:

setting the regulation target voltage to a first value to increase efficiency of operation of the internal controller; and setting the regulation target voltage to a second value higher than the first value to increase power delivery to the motor.

6. The method of claim 4, wherein, when a rectified voltage from the internal coil is above a voltage of the internal battery, the method further comprises:

selecting the internal coil as the power source; and setting the rectified voltage from the internal coil to be lower than the voltage of the internal battery.

7. A motor speed controller in an implanted medical device, the motor speed controller configured to maintain a speed of a motor of the implanted medical device within predefined limits of a target speed during a transient voltage signal, the motor speed controller comprising:

a first controller configured to:
track a first difference between the speed of the motor and the target speed, wherein a first latency is associated with the first controller tracking the first difference; and
produce a first signal indicative of the first difference;

a second controller configured to:
track a second difference between a target voltage and a supplied voltage, wherein a second latency is associated with the second controller tracking the second difference, and wherein the second latency is less than the first latency; and
responsive to a transient change in at least one of the speed of the motor or the supplied voltage, produce a second signal based on the second difference and based on the first signal; and a pulse width modulation (PWM) circuit configured to modulate the supplied voltage at a duty cycle determined by the second signal to produce a voltage applied to the motor to:
maintain the speed of the motor within the predefined limits of the target speed; and
drive the speed of the motor toward the target speed.

8. The motor speed controller of claim 7, wherein a source selected from an internal battery, an internal coil and a combination of the internal battery and internal coil provides the supplied voltage.

9. The motor speed controller of claim 7, wherein the PWM circuit is configured to increase the duty cycle when the supplied voltage decreases and to decrease the duty cycle when the supplied voltage increases.

10. The motor speed controller of claim 9, wherein, when the duty cycle of the PWM circuit exceeds a duty cycle threshold, the supplied voltage is increased.

* * * * *